(12) United States Patent
Dorok et al.

(10) Patent No.: US 8,778,512 B2
(45) Date of Patent: Jul. 15, 2014

(54) CHEMICAL COMPOUND FOR ORGANIC ELECTRONIC DEVICE AND ORGANIC ELECTRONIC DEVICE

(75) Inventors: Sascha Dorok, Dresden (DE); Ulrich Heggemann, Dresden (DE); Andrea Lux, Dresden (DE); Carsten Rothe, Dresden (DE)

(73) Assignee: Novaled AG, Dresden (DE)

( * ) Notice: Subject to any disclaimer, the term of this patent is extended or adjusted under 35 U.S.C. 154(b) by 428 days.

(21) Appl. No.: 13/291,169

(22) Filed: Nov. 8, 2011

(65) Prior Publication Data

US 2012/0119191 A1    May 17, 2012

(30) Foreign Application Priority Data

Nov. 16, 2010   (EP) .................................... 10191361

(51) Int. Cl.
| | | |
|---|---|---|
| H01L 51/50 | (2006.01) | |
| C07F 9/58 | (2006.01) | |
| C09K 11/06 | (2006.01) | |
| H01L 51/30 | (2006.01) | |
| H01L 51/40 | (2006.01) | |
| H01B 1/00 | (2006.01) | |

(52) U.S. Cl.
USPC ............... 428/690; 428/917; 427/58; 257/40; 257/E51.025; 257/E51.026; 546/21; 252/512; 252/514; 252/519.3

(58) Field of Classification Search
None
See application file for complete search history.

(56) References Cited

U.S. PATENT DOCUMENTS

| | | | |
|---|---|---|---|
| 5,093,698 | A | 3/1992 | Egusa |
| 6,013,384 | A | 1/2000 | Kido et al. |
| 6,589,673 | B1 | 7/2003 | Kido et al. |
| 7,074,500 | B2 | 7/2006 | Pfeiffer et al. |
| 7,776,455 | B2 | 8/2010 | Gerhard et al. |
| 2004/0227460 | A1 | 11/2004 | Liao et al. |
| 2006/0214565 | A1 | 9/2006 | Luo et al. |
| 2006/0227531 | A1 | 10/2006 | Iou |
| 2006/0250079 | A1 | 11/2006 | Kwok et al. |
| 2006/0269784 | A1 | 11/2006 | Ren et al. |
| 2007/0018154 | A1 | 1/2007 | Bae et al. |
| 2007/0138950 | A1 | 6/2007 | Yamamoto et al. |
| 2007/0185303 | A1 | 8/2007 | Stossel et al. |
| 2007/0196688 | A1 | 8/2007 | Ikeda et al. |
| 2007/0205411 | A1 | 9/2007 | Itai |
| 2007/0222373 | A1 | 9/2007 | Arakane et al. |
| 2007/0267970 | A1 | 11/2007 | Yamamoto et al. |
| 2008/0111473 | A1 | 5/2008 | Kawamura et al. |
| 2008/0203406 | A1 | 8/2008 | He et al. |
| 2008/0227979 | A1 | 9/2008 | Saalbeck et al. |
| 2008/0284325 | A1 | 11/2008 | Noh et al. |
| 2009/0001327 | A1 | 1/2009 | Werner et al. |
| 2009/0045728 | A1 | 2/2009 | Murano et al. |
| 2009/0212280 | A1 | 8/2009 | Werner et al. |
| 2009/0217980 | A1 | 9/2009 | Pfeiffer et al. |
| 2009/0235971 | A1 | 9/2009 | Pfeiffer et al. |
| 2009/0278115 | A1 | 11/2009 | Hosokawa et al. |
| 2010/0123390 | A1 | 5/2010 | Kamatani et al. |
| 2010/0157131 | A1 | 6/2010 | Kamatani et al. |
| 2011/0186864 | A1 | 8/2011 | Schwartz et al. |

FOREIGN PATENT DOCUMENTS

| | | |
|---|---|---|
| EP | 1 744 598 A1 | 1/2007 |
| EP | 2 072 517 A1 | 6/2009 |
| EP | 2 194 055 A1 | 6/2010 |
| JP | 2002063989 A | 2/2002 |
| JP | 2004095221 A | 3/2004 |
| WO | WO 03/088271 A1 | 10/2003 |
| WO | WO 2008/136583 A1 | 11/2008 |
| WO | WO 2005/073340 A1 | 8/2011 |

OTHER PUBLICATIONS

Lee et al., 2006, "Effects of hydroxyl groups in polymeric dielectrics on organic transistor performance," Applied Physics Letters, 88: p. No. 161209-1 to 161209-3.

Lee et al., 2009, "A phosphine oxide derivative as a universal electron transport material for organic light-emitting diodes" J. Mater. Chem., 2009, 19, 5940-5944.

Novosad et al., 2003, "The synthesis and characterization of three oxidized derivatives of bis(diphenylphosphino) pryidine and their Sn(IV) complexes," Polyhedron, 22:1585-1953.

Padmaperuma et al., "Phosphine Oxide Based Electron Transporting and Hole Blocking Materials for Blue Electrophosphorescent Organic Light Emitting Devices," Chem. Mater., 2010, 22 (20), pp. 5678-5686.

Wozniak et al., "Bis(trimethylsilyl)peroxide as a versatile reagent for selective generation of oxyphosphoryl group" Tetrahedron Letters, vol. 26, Issue 40, 1985, pp. 4965-4968.

Ziessel, 1989, "A new family of aromatic polyimine chelates substituted with two diphenylphosphines" tetrahedron Letters, 30(4):463-466.

*Primary Examiner* — Andrew K Bohaty
(74) *Attorney, Agent, or Firm* — Sutherland Asbill & Brennan LLP

(57) ABSTRACT

The present invention relates new compounds and to an organic electronic device comprising at least one substantially organic layer comprising a non fully conjugated chemical compound, which compound is preferably used in electron transport layers, electron injection layers. The invention also includes a process for preparing an organic electronic device, wherein the substantially organic layer comprising a non fully conjugated chemical compound is deposited on a first layer, and a second layer is deposited on the substantially organic layer, preferably a cathode being deposited on the substantially organic layer comprising the non fully conjugated chemical compound.

22 Claims, 2 Drawing Sheets

CHEMICAL COMPOUND FOR ORGANIC ELECTRONIC DEVICE AND ORGANIC ELECTRONIC DEVICE

CROSS-REFERENCE TO RELATED APPLICATIONS

This application hereby claims priority to European Patent Application No. 10 191 361.4, filed Nov. 16, 2010, the disclosure of which is expressly incorporated herein by reference.

FIELD OF THE INVENTION

The present invention relates to a chemical compound for an organic electronic device, an organic electronic device and a process for preparing thereof.

BACKGROUND OF THE INVENTION

Organic electronic devices, such as organic semiconductors, can be used to fabricate simple electronic components, e.g. resistors, diodes, field effect transistors, and also optoelectronic components like organic light emitting devices (e.g. organic light emitting diodes (OLED)), and many others. The industrial and economical significance of the organic semiconductors and their devices is reflected in the increased number of devices using organic semiconducting active layers and the increasing industry focus on the subject.

OLEDs are based on the principle of electroluminescence in which electron-hole pairs, so-called excitons, recombine under the emission of light. To this end the OLED is constructed in the form of a sandwich structure wherein at least one organic film is arranged as active material between two electrodes, positive and negative charge carriers are injected into the organic material and a charge transport takes place from holes or electrons to a recombination zone (light emitting layer) in the organic layer where a recombination of the charge carrier to singlet and/or triplet excitons occurs under the emission of light. The subsequent radiant recombination of excitons causes the emission of the visible useful light emitted by the light-emitting diode. In order that this light can leave the component at least one of the electrodes must be transparent. Typically, a transparent electrode consists of conductive oxides designated as TCOs (transparent conductive oxides), or a very thin metal electrode; however other materials can be used. The starting point in the manufacture of an OLED is a substrate on which the individual layers of the OLED are applied. If the electrode nearest to the substrate is transparent the component is designated as a "bottom-emitting OLED" and if the other electrode is designed to be transparent the component is designated as a "top-emitting OLED". The layers of the OLEDs can comprise small molecules, polymers, or be hybrid.

The most reliable and efficient OLEDs are OLEDs comprising doped layers. By electrically doping hole transport layers with a suitable acceptor material (p-doping) or electron transport layers with a donor material (n-doping), respectively, the density of charge carriers in organic solids (and therefore the conductivity) can be increased substantially. Additionally, analogous to the experience with inorganic semiconductors, some applications can be anticipated which are precisely based on the use of p- and n-doped layers in a component and otherwise would be not conceivable. The use of doped charge-carrier transport layers (p-doping of the hole transport layer by admixture of acceptor-like molecules, n-doping of the electron transport layer by admixture of donor-like molecules) in organic light-emitting diodes is, e.g., described in US 2008/203406 and U.S. Pat. No. 5,093,698.

All references to n-dopant or p-dopant in this patent application refer preferentially to the electrical dopants as described in the literature. The words dopant, doped, or doping refers to any inclusion of a guest material in a matrix material, preferentially to improve the electrical conductivity.

Several operational parameters of the OLED are being constantly improved to enhance the overall power efficiency. One important parameter is the operation voltage which can be tuned by improving the transport of charge carriers and/or reducing energy barriers such as the injection barriers from the electrodes. Other organic devices, such as organic solar cells also require improving in efficiency, which nowadays, are at best at about 8%.

Like an OLED, an organic solar cell has a stack of organic layers between two electrodes. In a solar cell, there must be at least one organic layer responsible for the absorption of light and a interface which separates the excitons created by the absorption (photo-active). The interface can be a bi-layer heterojunction, a bulk-heterojunction, or can comprise more layers, e.g., in a step wise interface. Also sensitizing layers and others can be provided. For increased efficiency, a good charge carrier transport is required, in some device structures the transport regions must not absorb light, therefore transport layers and photo-active layers may comprise different materials. Also charge carrier and/or excitors blocking layers may be employed. Highest efficiency solar-cells are, nowadays, multi-layer solar cells, some device structures are stacked (multi-junction solar cells) and connected by a connecting unit (also called recombination layer); nevertheless, single junction solar cells could have a high performance if the right materials were found. Examples of devices are given in US2009217980, or in US2009235971.

Differently than OLEDs and organic solar cells, transistors do not require doping of the entire semiconducting (channel) layer, because the concentration of available charge carriers is determined by an electric field supplied by a third electrode (gate electrode). However, convention organic thin film transistors (OTFTs) require very high voltages to operate. There is a need to lower this operating voltage; such an optimization can be done, e.g. with appropriate injection layers.

Organic transistors are also called organic field-effect transistors. It is anticipated that a large number of OTFTs can be used for example in inexpensive integrated circuits for non-contact identification tags (RFID) but also for screen control. In order to achieve inexpensive applications, generally thin-layer processes are required to manufacture the transistors. In recent years performance features have been improved to such an extent that the commercialization of organic transistors is foreseeable. For example, in OTFTs high field-effect mobilities of up to 6 cm2/Vs for electrons on the basis of C60 fullerene and up to 5.5 cm2/Vs for holes on the basis of pentacene (Lee et al., Appl. Lett. 88, 162109 (2006)) have been reported. A typical organic field-effect transistor comprises an active layer of organic semiconducting material (semiconducting layer) material which during the operation forms an electrical conduction channel, a drain and a source electrodes which exchange electrical charges with the semiconducting layer, and a gate electrode which is electrically isolated from the semiconducting layer by an dielectric layer.

There is a clear need to improve charge carrier injection and/or conductivity in organic electronic devices. Reducing or eliminating the barrier for charge injection between the electrode and the electron transport material (ETM) contributes strongly to enhancement of the device efficiency. Nowadays, there are two main approaches to reduce voltage and enhance efficiencies of organic electronic devices: improvement of the charge carrier injection and improvement of the conductivity of the transport layers. Both approaches can be used in combination.

For instance, U.S. Pat. No. 7,074,500 discloses a component structure for an OLED which leads to a greatly improved charge carrier injection from the electrodes into the organic layers. This effect is based on considerable band bending of the energy levels in the organic layer at the interface to the electrodes, as a result of which injection of charge carriers on the basis of a tunnel mechanism is possible. The high conductivity of the doped layers also prevents the voltage drop which occurs there during operation of the OLED. The injection barriers which may occur in OLEDs between the electrodes and the charge carrier transport layers are one of the main causes for an increase in the operating voltage compared to the thermodynamically justified minimum operating voltages. For this reason, many attempts have been made to reduce the injection barriers, for example by using cathode materials with a low work function, for example metals such as calcium or barium. However, these materials are highly reactive, difficult to process and are only suitable to a limited extent as electrode materials. Moreover, any reduction in operating voltage brought about by using such cathodes is only partial.

Metals having low work function, in particular alkali metals such as Li and Cs, are often used either as the cathode material or the injection layer to promote electron injection. They have also widely been used as dopants in order to increase the conductivity of the ETM, U.S. Pat. No. 6,013,384, U.S. Pat. No. 6,589,673. Metals such as Li or Cs provide a high conductivity in matrices which are difficult to dope otherwise (e.g. BPhen, Alq3).

However, the use of low work function metals has several disadvantages. It is well known that the metals can easily diffuse through the semiconductor, eventually arriving at the optically active layer quenching the excitons, thereby lowering the efficiency of the device and the lifetime. Another disadvantage is their high susceptibility to oxidation upon exposure to air. Therefore, devices using such metals as dopants, injection or cathode material require rigorous exclusion of air during production and rigorous encapsulation afterwards. Another well known disadvantage is that the molar doping concentration of the dopant must be close to 1:1, which strongly increase the undesired absorption of light of the transport layers. Yet another problem is their very high volatility leading to cross-contamination in the device assembling process making their use in device fabrication tools less attractive.

Another approach to facilitate metals as n-dopants and/or injection materials for ETM is the use of electron rich metal complexes and metal organic compounds, such as W(hpp)2 or Co(Cp*)2 (US2009/0212280, WO2003/088271) which have similar or slightly less doping/injecting ability in comparison with alkaline earth metals. Due to their still high enough electron donating capability, they are also undergoing rapid decay upon exposure to air, making their handling in device production difficult.

Yet another approach is the use of compounds of low work function metals in which the metal occurs in its oxidized stage. Inorganic compounds like LiF, NaCl, etc. have been used as well, these compounds do achieve some improvement, but cannot be used for devices with highest performance.

Hence, although compounds of alkaline earth metals are air stable, they are limited to the use as cathode material and only work in the injection approach, but not as a dopant which increases the conductivity of the matrix material.

Therefore, it is very desirable to provide new materials which possess high doping/charge injection capability allowing for highly efficient organic electronic devices substantially preserving the long-term stability of the device and which are infinitely stable in air.

It is therefore an objective of the present invention to provide a chemical compound, and an organic electronic device, preferably incorporating the chemical compound as a dopant or a charge injecting material, which overcomes state of the art limitations mentioned above and having improved performance compared to electronic devices of the prior art. Further, it is an object to provide a process for preparing such an organic electronic device.

BRIEF SUMMARY

The objects are achieved by the subject-matter of claims 1, 2 and 13. Preferred embodiments are disclosed in the subclaims.

The first object is achieved by a new chemical compound according to formula (I)

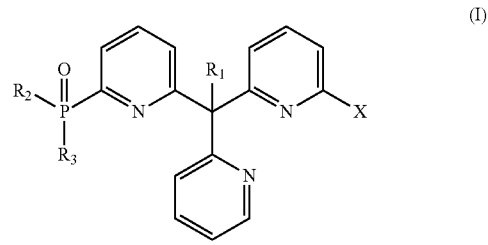

(I)

wherein
X is H or formula (I.2)

(I.2)

each R2-R3 is independently selected from H, linear and branched alkyl, preferably $C_1$-$C_6$-alkyl, aryl, preferably $C_6$-$C_{20}$-aryl, and heteroaryl, preferably $C_5$-$C_{20}$ heteroaryl; and R1 is independently selected from linear and branched alkyl, preferably $C_1$-$C_6$-alkyl, aryl, preferably $C_6$-$C_{20}$-aryl, and heteroaryl, preferably $C_5$-$C_{20}$ heteroaryl.

The chemical compound according to formula (I) is preferably a non-fully conjugated chemical compound.

Preferable compounds are those with the definition of formula (I) above wherein

R1 is selected from CH3, phenyl, pyridyl, picolyl, lutidyl, benzyl;

R2 and R3 are independently selected from substituted or non-substituted phenyl, naphthyl, anthryl, pyrenyl, fluorenyl, biphenylyl, phenanthryl, pyridyl;

R2 and R3 may be substituted, preferably by including substituents like alkyl, branched alkyl, aryl.

Another objective of the invention is achieved by an organic electronic device comprising at least one substantially organic layer comprising a chemical compound according to the definition above. Organic electronic devices according to the present invention are preferably organic light emitting devices or solar cells. Within inventive organic electronic devices, the chemical compound according to formula (I) can be used preferably as electron transport material, electron injection material, hole blocking material, exciton blocking material, dopant, and most preferably as dopant to increase the conductivity in an electron transport layer, optionally together with use of a metal and an electron transport material, as an injection layer material, or as a material for a pn junction.

DETAILED DESCRIPTION

Figure 1:
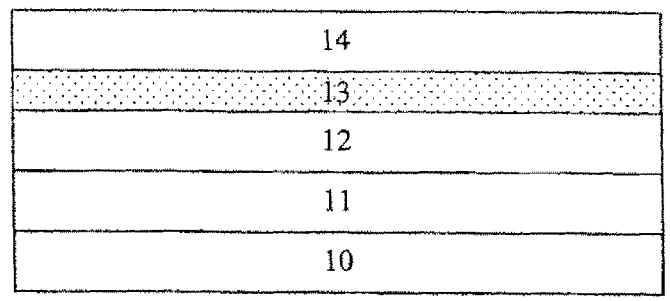
FIG. 1 illustrates a first embodiment of an inventive organic electronic device.

Preferred chemical compounds according to formula (I) with X=formula (I.2) can be selected from the following compounds (10)-(27):

| Compound | R1 | R2 | R3 |
|---|---|---|---|
| (10) | Ch3 | phenyl | phenyl |
| (11) | Ch3 | naphthyl | naphthyl |
| (12) | Ch3 | anthryl | anthryl |
| (13) | Ch3 | pyridyl | pyridyl |
| (14) | Ch3 | biphenylyl | biphenylyl |
| (15) | Ch3 | phenanthryl | phenanthryl |
| (16) | phenyl | phenyl | phenyl |
| (17) | phenyl | naphthyl | naphthyl |
| (18) | phenyl | anthryl | anthryl |
| (19) | phenyl | pyridyl | pyridyl |
| (20) | phenyl | biphenylyl | biphenylyl |
| (21) | phenyl | phenanthryl | phenanthryl |
| (22) | pyridyl | phenyl | phenyl |
| (23) | pyridyl | naphthyl | naphthyl |
| (24) | pyridyl | anthryl | anthryl |
| (25) | pyridyl | pyridyl | pyridyl |
| (26) | pyridyl | biphenylyl | biphenylyl |
| (27) | pyridyl | phenanthryl | phenanthryl |

Other preferred compounds are based on the table above and Formula (I) with X=H.

Individual steps of the synthetic procedure, for instance, the synthesis of the diphenylphosphin-substituent are described in R. Ziesel, Tetrahedron Letters, 1989, 30(4), 463-466; Asanga B. Padmaperuma et. al.; Chem. Mater., 2010, 22, 5678-5686 (including oxidation); Jun Yeob Lee et al., Journal of Materials Chemistry, 2009, 19, 5940-5944 (including oxidation). The oxidation of phosphines to phosphine oxides is described in L. Wozniak, J. Kowalski, J. Chojnowski; Tetrahedron Letters, 1985, 26(40), 4965-4968; J. Novosad et. al.; Polyhedron. 2003, 22, 1585-1593.

The synthesis is described by the following examples:
Compound (28):

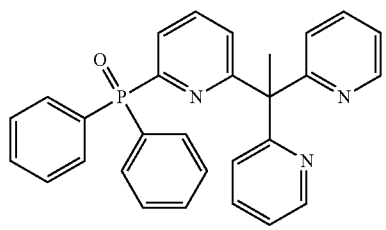 [SMILES: CC(c1ccccn1)(c1ccccn1)c1cccc(P(=O)(c2ccccc2)c2ccccc2)n1]

Synthesis of (6-(1,1-di(pyridin-2-yl)ethyl)pyridin-2-yl)diplienylphosphine oxide 1. 2,2'-(ethane-1,1-diyl)dipyridine 58.0 g (540 mmol) of 2-ethylpyridin were dissolved in 550 ml tetrahydrofurane and cooled to −80° C. 200 ml (540 mmol) of butyl lithium (2.7 M in heptane) were added over a period of thirty minutes. After stirring at −20° C. for two hours 26.3 g (270 mmol) of 2-fluoropyridine were added. The mixture was stirred under reflux for thirty minutes, then cooled and poured on 500 ml ice. The layers were separated and the aqueous layer was extracted with 200 ml dichloromethane. The combined organic layers were dried with sodium sulphate and concentrated under reduced pressure. The oily residue was distilled under reduced pressure to yield 39.8 g (80%) of yellow oil that was used in the next synthesis without further purification.

2. 2,2'-(1-(6-fluoropyridin-2-yl)ethane-1,1-diyl)dipyridine 26.8 g (145 mmol) of 2,2'-(ethane-1,1-diyl)dipyridine were dissolved in 400 ml of tetrahydrofurane. A solution of 32 g (160 mmol) of potassium hexamethyldisilazide in 240 ml tetrahydrofuran was added. Meanwhile the solution coloured to dark red. After stirring for one hour 16.8 g (145 mmol) of 2,6-difluoropyridine was added in one batch. The mixture was heated under reflux for 1 hour.

After cooling down to room temperature the mixture was quenched with 400 ml of saturated ammonium chloride solution and the solvent was removed under reduced pressure. 400 ml of ethyl acetate and 400 ml water were added to the residue and the aqueous layer was washed with 100 ml of ethyl acetate. The combined organic layers were washed with brine, dried with sodium sulphate, filtrated and concentrated. The solid residue was stifled with 200 ml tert-butyl methyl ether over night. The solid was filtrated and dried at 40° C. in vacuum to yield 36.6 g (90%) of a white powder, that was used in the next synthesis without further purification.

3. 2,2'-(1-(6-(diphenylphosphino)pyridin-2-yl)ethane-1,1-diyl)dipyridine 39.5 ml (19.8 mmol) of potassium diphosphide (0.5 M solution in tetrahydrofurane) were dissolved in 55 ml of tetrahydrofurane and cooled to −50° C. A solution of 5.0 g (18.0 mmol) of 2,2'-(1-(6-fluoropyridin-2-yl)ethane-1,1-diyl) dipyridine in 25 ml tetrahydrofurane was added and the mixture was stirred for 16 hours at room temperature. The solvent was evaporated under reduced pressure and the residue was dissolved in 200 ml of ethyl acetate and hydrolysed with 100 ml of saturated ammonium chloride solution. The aqueous layer was extracted with ethyl acetate. The combined organic layers were washed two times with saturated sodium chloride solution and dried with sodium sulphate solvent was removed under reduced pressure to yield 7.00 g (88%) of crude product which was used in the next synthesis without further purification.

4. (6-(1,1-di(pyridin-2-yl)ethyl)pyridin-2-yl)diphenylphosphine oxide 6.7 g of 2,2'-(1-(6-(diphenylphosphino)pyridin-2-yl)ethane-1,1-diyl)dipyridine were dissolved in 25 ml of dichloromethane and ice-bath cooled. 1.8 ml of hydrogen peroxide (35 wt % in water) were added drop wise and the mixture was stirred overnight at room temperature. The reaction was quenched with 20 ml of saturated ammonium chloride solution and the aqueous layer was extracted three times with dichloromethane. The combined organic layers were washed with brine and dried with magnesium sulphate. The solvent was removed under reduced pressure until the residue starts to foam. The residue crystallised from diethyl ether. After drying in high vacuum 5.1 g (74%) of an off-white solid were obtained. The compound was further purified by gradient sublimation.

Compound (10):

Synthesis of (6,6'-(1-(pyridin-2-yl)ethane-1,1-diyl)bis(pyridine-6,2-diyl))bis diphenylphosphine oxide)

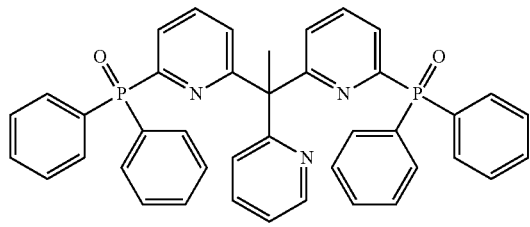

(10)

1. 6,6'-(1-(pyridin-2-yl)ethane-1,1-diyl)bis(2-fluoropyridine)

13.8 g (129 mmol) of 2-ethylpyridine were dissolved in 220 ml of water-free tetrahydrofurane and cooled to −80° C. 100 ml (270 mmol) of butyllithium (2.7 M solution in heptane) were added via a double needle over a period of 30 min. Meanwhile the solution coloured to dark red. After warming the mixture to −50° C. a solution of 13.6 ml (257 mmol) 2,6-difluoropyridine in 190 ml THF was added. The mixture was heated under reflux for 4 hours.

After cooling down to room temperature the mixture was quenched with 280 ml of saturated ammonium chloride solution and the organic solvent was removed under reduced pressure. 500 ml of diethylether and 300 ml water were added to the residue and the aqueous layer was washed five times with 200 ml of ethylacetate. The combined organic layers were washed three times with 100 ml of saturated sodium chloride solution, dried with sodium sulphate, filtrated and concentrated. The residue was washed twice with 50.0 ml of isopropanol and then filtrated. The mother liquor was concentrated, stored at −0° C. overnight and filtrated. The residue was washed with small amounts of isopropanol. The combined solids were dried at 30° C. in vacuum over night.

19.26 g (51%) product were obtained as a slightly yellow coloured solid that was used in the next synthesis without further purification.

2. 6,6'-(1-(pyridin-2-yl)ethane-1,1-diyl)bis(2-(diphenylphosphino)pyridine)

14.0 g (48.0 mmol) of 6,6'-(1-(pyridin-2-yl)ethane-1,1-diyl)bis(2-fluoropyridin) were dissolved in 300 ml of tetrahydrofurane and cooled to −60° C. 200 ml (100 mmol) of potassium diphenylphosphide (0.5 M solution in tetrahydrofurane) were added and the mixture was stirred for three days at room temperature. The reaction was hydrolysed with 200 ml of saturated ammonium chloride solution. The aqueous layer was extracted three times with ethyl acetate. The combined organic layers were washed two times with saturated ammonium chloride solution and dried with sodium sulphate. The solvent was removed under reduced pressure to yield 40 g (>100%) of crude product which was used in the next synthesis without further purification.

3. (6,6'-(1-pyridin-2-yl)ethane-1,1-diyl)bis(pyridine-6,2-diyl))bis(diphenylphosphine oxide)

40.0 g of 6,6'-(1-(pyridine-2-yl)ethane-1,1-diyl)bis(2-(diphenylphosphino)pyridine) were dissolved in 500 ml of dichloromethane and ice-bath cooled. 14.7 ml of hydrogen peroxide (35 wt % in water) were added drop wise and the mixture was stirred overnight at room temperature. The reaction was quenched with 150 ml of saturated ammonium chloride solution and the aqueous layer was extracted two times with dichloromethane. The combined organic layers were washed two times with brine and dried with sodium sulphate. The solvent was removed under reduced pressure to yield an oily residue. The residue was stirred with a mixture of diethyl ether and hexane, filtrated and washed with hexane and ethyl ether. The washing procedure was repeated with methyl tert-butyl ether and hot ethyl acetate. The product was crystallised from a dichloromethane hexane mixture. After drying at 40° C. in vacuum 22.0 g (70%) of an off-white solid were obtained. The compound was further purified by gradient sublimation.

Variations of R2 and R3 of compounds (10) and (28) can be easily made for instance by replacing the potassium diphenylphosphide by another phosphide like alkali salts of: diphenyl, ditolylphosphide, dixylylphosphide, dimesitylphosphide, dinaphthylphosphide, dianthrylphosphide, di(biphenyl)phosphide, diphenanthrylphosphide, dipyridylphosphide.

Variations of R1 of compounds (10) and (28) can be made by replacing the starting material 2-ethylpyridine by another suitable material.

Preferably the compound according to formula (I) is used in transport and/or injection layers.

These compounds according to formula (I) have a high energy band-gap and are not fully conjugated. The chemical compounds according to formula (I) are air-stable and capable to be evaporated without decomposition. They are also soluble in a variety of solvents. This makes the compounds according to formula (I) particularly easy to use in manufacturing processes.

In a further development of the invention, the substantially organic layer comprises at least one metal or a metal ion, preferably interacting with the chemical compound according to formula (I), wherein the metal or metal ion is preferably selected from Ag, Al, Mg, Ba, Ca, Yb, In, Zn, Sn, Sm, Bi, Eu, Li, more preferably from Al, Mg, Ca, Ba and even more preferably selected from Al or Mg.

It is preferred that the molar ratio of metal: compound according to formula (I) is 1:1 or less, so that there is no excess metal in the layer.

The inventive organic electronic device preferably comprises a layered structure including a substrate, an anode and a cathode, the at least one substantially organic layer being disposed within the layered structure between the anode and the cathode.

Preferably, the cathode comprises a metal selected from Ag, Al, Mg, Ba, Ca, Yb, In, Zn, Sn, Sm, Bi, Eu, Li, more preferably from Al, Mg, Ca, Ba and even more preferably selected from Al or Mg. Preferred is also a cathode comprising an alloy of Mg and Ag.

In one preferred embodiment, the cathode is a top electrode and the anode is a bottom electrode, wherein the bottom electrode is closer to the substrate than the top electrode.

Even preferred the substantially organic layer has an interface with the cathode.

The substantially organic layer may further comprise an electron transport material. The electron transport material constitutes preferably 10 wt % or more of the substantially organic layer. This is to allow charge transport through the layer. More preferred is 40% or more. For an electron transport layer, it is more preferred that the electron transport material is the main component of the layer.

Suitable matrix materials as electron transport materials can be as follows:

As matrix materials for electron transport layers, use may be made for example of fullerenes, such as for example C60, oxadiazole derivatives, such as for example 2-(4-biphenyl)-5-(4-tert-butylphenyl)-1,3,4-oxadiazole, quinoline-based compounds such as for example bis(phenylquinoxalines), or oligothiophenes, perylene derivatives, such as e.g. perylenetetracarboxylic acid dianhydride, naphthalene derivatives such as e.g. naphthalenetetracarboxylic acid dianhydride, or other electron transport materials.

As matrix materials for electron transport layers, use may also be made of quinolinato complexes, for example of aluminum or other main group metals, it also being possible for the quinolinato ligand to be substituted. In particular, the matrix material may be tris(8-hydroxy-quinolinato)aluminum. Other aluminum complexes with O and/or N donor atoms may optionally also be used. The quinolinato complexes may contain for example one, two or three quinolinato ligands, the other ligands preferably complexing with O and/or N donor atoms on the central atom, such as for example the following Al complex.

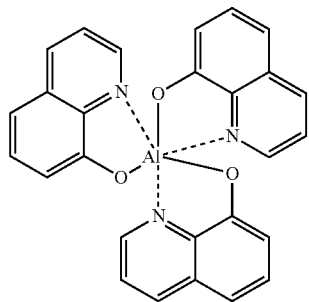

tris[8-hydroxyquinolinato] aluminum(III)

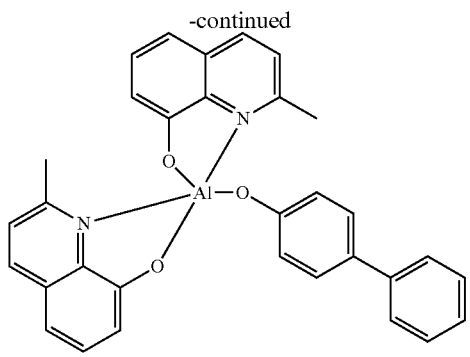

bis(2-methyl-8-quinolinato)-4-phenylphenolato) aluminum(III)

As matrix materials, use may also be made of heteroaromatics such as, in particular, triazole derivatives, optionally also pyrroles, imidazoles, triazoles, pyridines, pyrimidines, pyridazines, quinoxalines, pyrazino-quinoxalines and the like. The heteroaromatics are preferably substituted, in particular aryl-substituted, for example phenyl- or naphthyl-substituted. In particular, use may be made of the following triazole as matrix material.

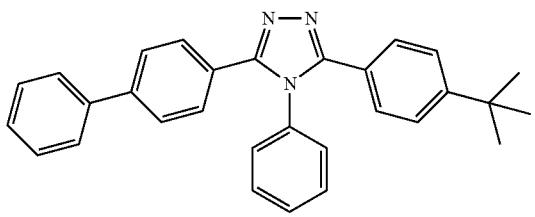

3-(4-biphenylyl)-4-phenyl-5-tert.-butylphenyl-1,2,4-triazole

Other compounds suitable as electron transport materials are compounds from:

US2007/0138950, preferentially, compounds (1) and (2) on page 22, compounds (3), (4), (5), (6), and (7) on page 23, compounds (8), (9), and (10) on page 25, and compounds (11), (12), (13), and (14) on page 26, which compounds are incorporated herein by reference;

US2009/0278115 A1, preferentially, compounds (1) and (2) on page 18, which compounds are incorporated herein by reference;

compounds from US2007/0018154, preferentially the compounds of claim 10, formula 1-1, 1-2, 1-3, 1-4, 1-5, 1-6 on page 19, 1-7 to 1-146 on pages 20 to 26. Compounds from US2008/0284325 A1, preferentially compounds on page 4: 2-(4-(9,10-diphenylanthracen-2-yl)phenyl)-1-phenyl-1H-benzo[d]imidazole, 2-(4-(9,10-di([1,1'-biphenyl]-2-yl)anthracen-2-yl)phenyl)-1-phenyl-1H-benzo[d]imidazole, 2-(4-(9,10-di(naphthalen-1-yl)anthracen-2-yl) phenyl)-1-phenyl-1H-benzo[d]imidazole, 2-(4-(9,10-di(naphthalen-2-yl) anthracen-2-yl)phenyl)-1-phenyl-1H-benzo[d]imidazole, 2-(4-(9,10-di([1,1':3',1''-terphenyl]-5'-yl)anthracen-2-yl) phenyl)-1-phenyl-1H-benzo[d]imidazole, and the compound on page 5, which compounds are incorporated herein by reference;

naphthacene derivatives from US2007/0222373, preferentially, compounds (A-1) and (A-2) from page 17, compounds (A-3) from page 18 and (A-4) from page 19, which compounds are incorporated herein by reference;

compounds from US2008/0111473, preferentially, compound 1 on page 61, compound 2 on page 62, compounds 3 and 4 on page 63, compound 5 on page 64, and compound 6 on page 65, which compounds are incorporated herein by reference;

compound H-4 from page 20, and compounds (1) and (2) of page 12 of US2010/0157131, which compounds are incorporated herein by reference;

compounds from US2010/0123390, according to general formula (1), preferentially, compounds H4, H5 p.21, H7 p.22, H11, H12, H13 p.23, H16, and H18 p.24, which compounds are incorporated herein by reference;

US2007/0267970, preferentially 2-([1,1'-biphenyl]-4-yl)-1-(4-(10-(naphthalen-2-yl)anthracen-9-yl)phenyl)-2,7a-dihydro-1H-benzo[d]imidazole (compound 1). 2-([1,1'-biphenyl]-2-yl)-1-(4-(10-(naphthalen-2-yl)anthracen-9-yl)phenyl)-2,7a-dihydro-1H-benzo[d]imidazole (compound 2). Compound (C-1) from US2007/0196688, p. 18, which is incorporated herein by reference;

Additional known electron transport materials can be used such as: 1,3,5-Tris(1-phenyl-1H-benzimidazol-2-yl)benzene; 2-(4-Biphenylyl)-5-phenyl-1,3,4-oxadiazol; Tris(2,4,6-trimethyl-3-(pyridine-3-yl)phenyl)borane; 4,4'-bis(4,6-diphenyl-1,3,5-triazin-2-yl)biphenyl; 2,2'-Di-pyrenyl-9,9-spirobifluorene; 9,9-Bis[-pyrenyl)phenyl]fluorine; 2,2'-Bi(9,10-dipheny-lanthracene); Triphenylphosphinoxid; 14-phenyldibenzo[a,j]acridine; 2,7-Di-pyrenyl-9,9-spirobifluorene; 7-(naphthalene-2-yl)dibenzo[c,h]acridine; rubrene; phenyldi(pyren-1-yl)phosphine oxide; anthracene.

Other preferred compounds as matrix materials for the electron transport layer are phenanthrolines and substituted phenanthrolines such as 4,7-diphenyl-1,10-phenanthroline, 2,9-dimethyl-4,7-diphenyl-1,10-phenanthroline, 2,9-di(naphthalen-2-yl)-4,7-diphenyl-1,10-phenanthroline, 4-(naphthalen-1-yl)-2,7,9-triphenylpyrido[3,2-h]quiriazoline, 2,9-bis(4-methoxyphenyl)-4,7-diphenyl-1,10-phenanthroline, 2,9-di(naphthalen-1-yl)-4,7-diphenyl-1,10-phenanthroline, the compounds according to formula I on page 3 of US 2009/0001327 A1, compounds according to formulas II and III on page 3 of US 2009/0001327 A1, compounds according to "Struktur 8" on page 5 of EP2072517 A1, compounds according to the formula on paragraph 28 on page 5 of EP2194055 A1, which compounds and references are all incorporated herein by reference.

Particularly preferred the electron transport material is selected from:

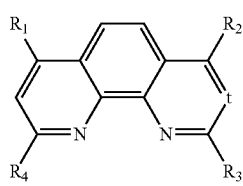

Formula (2)

wherein R1-R4 are independently selected from H, C1-C20-Alkyl, branched C4-C20-alkyl or C3-C20-cycloalkyl, C1-C20 alkenyl, C1-C20 alkinyl, aryl preferably selected from phenyl, tolyl, biphenylyl, naphthyl, or heteroaryl preferably selected from pyridyl, pyrimidinyl, quinolinyl, pyrazinyl, thiophenyl, furanyl, benzothiophenyl, benzoluranyl;

wherein the structural element t is selected from CH, CR1, N, CCN.

Preferred examples of an electron transport material are as follows: 2,9-di([1,1'-biphenyl]-4-yl)-4,7-di-p-tolyl-1,10-phenanthroline; 2,9-di(phenanthren-2-yl)-4,7-diphenyl-1,10-phenanthroline; 2,9-di([1,1':4',1''-terphenyl]-4-yl)-4,7-diphenyl-1,10-phenanthroline; 2,9-bis(1,1'-dimethyl-9H-fluoren-2-yl)-4,7-diphenyl-1,10-phenanthroline; 2,9-bis(4'-(tert-butyl)-[1,1'-biphenyl]-4-yl)-4,7-di-p-tolyl-1,10-phenanthroline; 2,9-di([1,1':4',1''-terphenyl]-4-yl)-4,7-di-p-tolyl-1,10-phenanthroline; 2,9-bis(4'-(tert-butyl)-[1,1'-biphenyl]-4-yl)-4,7-diphenyl-1,10-phenanthroline; 2,4,7,9-tetra([1,1'-biphenyl]-4-yl)-1,10-phenanthroline; 2,9-di([1,1'-biphenyl]-4-yl)-4,7-di(naphthalen-1-yl)-1,10-phenanthroline; 2,9-di([1,1'-biphenyl]-4-yl)-4,7-di(naphthalen-2-yl)-1,10-phenanthroline; 2,9-di([1,1'-biphenyl]-4-yl)-4,7-bis(4-(thiophen-2-yl)phenyl)-1,10-phenanthroline; 2,9-di([1,1'-biphenyl]-4-yl)-4,7-bis(4-(pyrimidin-2-yl)phenyl)-1,10-phenanthroline.

It will be understood that the aforementioned matrix materials may also be used in a mixture with one another or with other materials in the context of the invention. It will be understood that use may also be made of suitable other organic matrix materials which have semiconductor properties.

In another preferred embodiment, the substantially organic layer is present in a pn junction, the pn junction having at least two layers, namely a p- and n-layer, and optionally an interlayer i in between, wherein the interlayer i and/or the n-layer is (are) the substantially organic semiconducting layer.

The organic electronic device may additionally comprise a polymer semiconducting layer.

Most preferably, the organic electronic device is a solar cell or a light emitting diode.

The organic electronic device may be also a field effect transistor comprising a semiconducting channel, a source electrode, and a drain electrode, the substantially organic layer being provided in between the semiconducting channel and at least one of the source electrode and the drain electrode.

In a further most preferred embodiment, the substantially organic layer comprising the chemical compound according to formula (I) is an electron injection layer and/or a n-doped electron transport layer.

The second object is achieved by a process for preparing an inventive organic electronic device wherein the substantially organic layer comprising a chemical compound according to formula (I) is deposited on a first other layer, and a second other layer is deposited on the substantially organic layer, preferably a cathode being deposited on the substantially organic layer comprising the chemical compound according to formula (I).

Preferably, the substantially organic layer may be evaporated, preferably co-evaporated with metal and/or electron transport material.

Alternatively, the substantially organic layer is formed from a solution.

In other words, any layers of the inventive organic electronic device, especially the substantially organic layer can be deposited by known techniques, such as vacuum thermal evaporation (VIE), organic vapour phase deposition, laser induced thermal transfer, spin coating, blade or slit coating, inkjet printing, etc. A preferred method for preparing the organic electronic device according to the invention is vacuum thermal evaporation.

Surprisingly, it was found that the inventive organic electronic device overcomes disadvantages of prior art devices and has in particular an improved performance compared to electronic devices of the prior art, for example with regard to efficiency.

Organic electronic devices according to the invention are also preferred having connecting units. Multiple stacks of organic layers comprising an optoelectronic-active unit such as an emitter unit of an OLED or an absorbing unit of an organic solar cell can be stacked upon each other to form a tandem (in case of 2 units) or stacked device (in case of 2 or more units). A connecting unit must be provided between each optoelectronic-active unit, many different approaches for such connecting units are known: doped organic pn junctions are described in US 2009045728; pn junctions with a metal interlayer are shown in US 2004227460 and US 2007205411; completely inorganic junctions are described in US 2006214565, US 2006250079, and US 2006227531. Such connecting units are also called pn junctions, charge generation layer when used in OLEDs; or charge recombination layer when used in solar cells. There is no complete description about how such a connecting unit works, for some structures it is possible that the working principle is similar to a tunnel junction. A connecting unit can also be used between an electrode and an optoelectronic-active unit, as disclosed e.g. in FP 1 808 910.

Organic electronic devices according to the invention are preferred having connecting units (pn junctions) utilizing the chemical compound according to formula (I) as dopant 1 as follows:
  dopant1:ETL/p-dopant/HTL
  ETL (with or without dopant1)/dopant1:/HTL
  (with or without dopant1) ETL/p-doped HTL
  dopant1:ETL/p-dopant/HTL
  (with or without dopant1)ETL/dopant1/p-doped HTL
  (with or without dopant1)ETL/p-doped HTL
  dopant1:ETL/HTL
  dopant1:ETL/p-doped HTL Additionally, it is preferred that the substantially organic layer is present in a pn junction, wherein the organic layer is used as interlayer (i) as follows:
  ETL/i/p-dopant/HTL
  ETL/n-dopant/i/HTL
  ETL/i/p-doped HTL
  n-doped ETL/i/p-dopant/HTL
  ETL/n-dopant/i/p-doped HTL
  ETL/i/p-doped
  n-doped ETL/i/HTL
  n-doped ETL/i/p-doped HTL It is also preferred to use the substantially organic layer in pn junctions in combination with a metal or metal ion in one of the layers. The metal or metal ion in the pn junction is preferably selected from Ag, Al, Mg, Ba, Ca, Yb, In, Zn, Sn, Sm, Bi, Eu, Li, more preferably from Al Mg, Ca, Ba and even more preferably selected from Al or Mg.

A preferred pn junction comprises the layer structure: dopant1 (mixed or preferentially pure layer)/thin metal layer (pure layer with thickness <5 nm);

In one embodiment, the combination of the substantially organic layer with a metal or metal ion is carried out by mixing the metal into at least one of the following layers: the ETL and layer comprising dopant. In another preferred embodiment, the ETL and/or layer comprising dopant are formed adjacent to a thin metal layer (thickness 0.5 nm to 5 nm).

Injection Layer

In a preferred embodiment, the substantially organic layer, having the compound according to formula (I) as its main component, is adjacent to a cathode, preferably between a cathode and one of an ETL or HBL (hole blocking layer). The present invention has the advantages that, especially for non-inverted structures, the simplest form is also the one with a significantly improved performance compared to the structure not using an injection layer. The compound according to formula (I) can be used as a pure layer and is then preferably the only layer between an electron transporting layer (ETL or HBL) and the cathode. In this regard it is preferred for an OLED that the EML (emitter layer) and ETL matrix can be the same if the emission zone is far from the cathode. For a solar cell, the acceptor used in the optically active layer (such as C60) can be also a matrix for the ETL.

Such a pure layer as injection layer in organic electronic devices has a preferable thickness between 0.5 nm and 5 nm.

The thickness of the layer comprising the compound according to formula (I) is the nominal thickness, such thickness is usually calculated from the mass deposited on a certain area by the knowledge of the material's density. For example, with vacuum thermal evaporation VTE, the nominal thickness is the value indicated by the thickness monitor equipment. In reality, since the layer is not homogeneous and not flat at least at one interface, its final thickness is difficult to measure, in this case, the average value can be used. The cathode in this regard is a conductive layer having optionally any surface modifications to modify its electrical properties, e.g. to improve its work-function or conductivity. Preferably, the cathode is a double layer, more preferably it is a single layer to avoid complexity.

In another preferred embodiment, the organic layer comprises the chemical compound according to formula (I) and a metal, this layer being then preferably adjacent to the cathode (and there is no other layer in between) and favors injection in the organic semiconductor.

Semiconducting Layer

It was further found that the compound according to formula (I) has a very high energy gap, therefore it can be mixed in small amounts in any semiconducting layer without modifying the semiconductor properties of that layer in a significant extent. Small amounts refer to concentrations of less than 30 mol-%, preferably less than 10 mol-%. In another preferred embodiment, the organic layer may be a transport or blocking layer such as a hole transport layer, an electron transport layer, a hole blocking layer or an electron blocking layer.

It is even preferred that the organic layer is an electron transport layer adjacent to the cathode and comprising the compound according to formula (I). If the ETL is directly adjacent to the cathode, this simplification has the advantage that no additional injection layer is required. Alternatively, an additional injection layer can be provided between the ETL and the cathode. This additional layer can be a layer having the chemical compound according to formula (I) as its main component, as already illustrated above. In one even preferred embodiment, the ETL is beneath the cathode (no other layer in between) wherein the cathode is the top electrode, which is formed after forming the ETL (non-inverted structure).

As already mentioned above, the substantially organic layer can be preferably an electron transport layer comprising a metal. Such a layer can be produced, for example, with vacuum thermal evaporation, simultaneously evaporating the electron transport material, the chemical compound according to formula (I) and a metal.

Such a layer increases the conductivity of electron transport layers significantly. Surprisingly, high conductivities were obtained using electron transport matrix materials which are otherwise not easily to be doped. The metals can be incorporated by many known techniques. An additional effect that was observed is an improvement of the OLED and also of the solar cell lifetime; and this improvement is better than the improvement expected only due to doping.

Polymer Hybrid OLED or Solar Cell

In a further preferred embodiment the substantially organic layer comprising the chemical compound according to formula (I) is used in combination with a polymer semiconductor, preferably between a cathode and a polymer layer, wherein the polymer layer preferably comprises the optoelectronic active region of the device (emitting region of an OLED or the absorbing region of a solar cell). All alternatives of layers comprising the chemical compound according to formula (I) or being composed thereof can be used in combination with that polymer layer. Exemplary alternative layers can be an injection layer being composed of the chemical compound according to formula (I), an injection layer comprising the chemical compound and a metal, an electron transport layer having the chemical compound with or without a metal. The electronic interface to the cathode is then strongly improved given the high electron injection capability of the chemical compound (I).

Electrical Doping

The invention can be used in addition to conventional doping of organic semiconducting layers. By using the term doping it is meant electrical doping as explained above. This doping can also be called redox-doping or charge transfer doping. It is known that the doping increases the density of charge carriers of a semiconducting matrix towards the charge carrier density of the undoped matrix. An electrically doped semiconductor layer also has an increased effective mobility in comparison with the undoped semiconductor matrix.

US2008227979 discloses in detail the doping of organic transport materials, also called ma-trix, with inorganic and with organic dopants. Basically, an effective electronic transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of doped hole transport materials are: copperphthalocyanine (CuPc), which HOMO level is approximately −5.2 eV, doped with tetrafluoro-tetracyanoquinonedimethane (F4TCNQ), which LUMO level is about −5.2 eV; zincphthalocyanine (ZnPc) (HOMO)=−5.2 eV) doped with F4TCNQ; a-NPD (N,N'-Bis(naphthalen-1-yl)-N,N'-bis(phenyl)-benzidine) doped with F4TCNQ.

Typical examples of doped electron transport materials are: fullerene C60 doped with acridine orange base (AOB); perylene-3,4,9,10-tetracarboxylic-3,4,9,10-dianhydride (PTCDA) doped with leuco crystal violet; 2,9-di(phenanthren-9-yl)-4,7-diphenyl-1,10-phenanthroline doped with tetrakis(1,3,4,6,7,8-hexahydro-2H-pyrimido[1,2-a]pyrimidinato) ditung-sten (II) (W(hpp)4); naphthalene tetracarboxylic acid di-anhydride (NTCDA) doped with 3,6-bis-(dimethyl amino)-aeridine; NTCDA doped with bis (ethylene-dithio)tetrathiafulvalene (BEDT-TTF).

OTFT

The inventive organic electronic device also allows the provision of improved organic thin film transistors (OTFT). This requires an injection layer between the source electrode and the semiconducting layer, and between the drain electrode and semiconducting layer. In such an OTFT the injection layer may be the substantially organic layer comprising the chemical compound according to formula (I). In this regard, it is preferred that the substantially organic layer is a pure layer of the chemical compound according to formula (I), more preferably in direct contact to the drain and source, i.e. no other layers inbetween. Such a layer can be interrupted (only under the electrodes) or not (unstructured). Because the lateral displacement of drain and source electrode is very small, the injection layer needs to be patterned with high precision. This constrain is relaxed with the use of non-patterned injection layers, however, common non-patterned injection layers also cover the semiconducting layer in the channel region, which may dope the channel region and may have the undesired effect to increase the off current of the transistor.

It was found that such an undesired effect does not occur for inventive organic electronic devices, due to high HOMO-LUMO energy gap they do not disturb or modify the electrical properties of the semiconductor. Due to the contact to the source and drain electrodes, a good injection layer is provided. This effect is enhanced if the source and drain electrodes are deposited over the injection layer. Therefore, it is preferred to use an injection layer comprising the chemical compound according to formula (I), wherein the injection layer is formed between the electrodes and the semiconductor and is unpatterned in the region between source and drain. The preferred thickness of such an injecting layer is below 5 nm.

In addition, or alternatively, the substantially organic layer can be used as a thin layer between the dielectric and the semiconductor, In addition, or alternatively, the semiconductor layer can comprise small concentrations of the chemical compound (I), preferably less than 30 mol-% or preferably less than 10 mol-%. Preferably, the semiconducting layer and the inventive compound are in a layer as a homogeneous mixture.

Organic Electronic Devices

FIG. 1 illustrates a first embodiment of an inventive organic electronic device in the form of a stack of layers forming an OLED or a solar cell. In FIG. 1, 10 is a substrate, 11 is an anode, 12 is an EML or an absorbing layer, 13 is a EIL, 14 is a cathode.

The layer 13 can be a pure layer of a compound according to formula (I), alternatively it can also comprise a metal, which metal can also be used in the cathode material. At least one of the anode and cathode is at least semi-transparent. Inverted structures are also foreseen (not illustrated), wherein the cathode is on the substrate (cathode closer to the substrate than the anode and the order of the layers 11-14 is reversed). In this case, it is preferred that the layer 13 also comprises a metal. The stack may comprise additional layers, such as ETL, HTL. etc.

Figure 2:
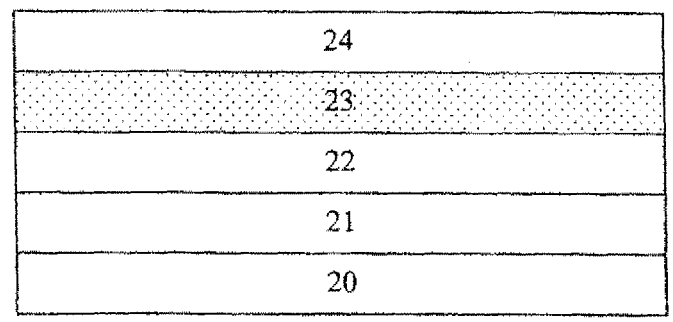
FIG. 2 illustrates a second embodiment of an inventive organic electronic device.

FIG. 2 represents a second embodiment of the inventive organic electronic device in the form of a stack of layers forming an OLED or a solar cell. Here, 20 is a substrate, 21 is an anode, 22 is an EML or an absorbing layer, 23 is an 24 is a cathode. The layer 23 comprises an electron transport matrix material and a compound according to formula (I). In addition, layer 23 may also comprise a metal.

Figure 3:
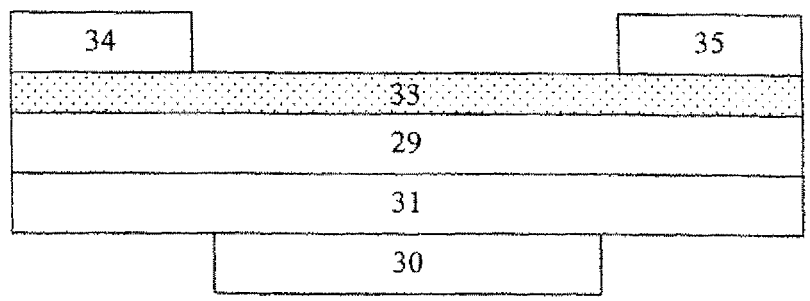
FIG. 3 shows a third embodiment of an inventive organic electronic device.

FIG. 3 illustrates a third embodiment of the inventive device in the form of an OTFT, with a semi-conductor layer 32, a source electrode 34 and a drain electrode 35. An unpatterned (unpatterned in between the source and drain electrodes) injection layer 33 provides charge carrier injection and extraction between the source-drain electrodes and a semi-conducting layer. OTFT also comprises a gate insulator 31 (which could be on the same side as the source-drain electrodes) and a gate electrode 30, which gate electrode 30 is on the side of the layer 31 which is not in contact with the layer 32. Obviously the whole stack could be inverted. A substrate may also be provided, or alternatively, the insulator layer 31 may be the substrate.

The following examples were prepared utilizing always the same compound to enable direct comparison of the performance. Of course, any compound according to formula (I) can be used. On sets of experiments realized in batches of parallel organic electronic devices, it was found that all compounds according to formula (I) in a substantially organic layer of an organic electronic device provided an increased performance.

EXAMPLES

Example 1.1

Electron Injection

Devices were prepared to determine the electron injection properties of the invented compounds, the experiment with compound (10) is presented in the following. An electron only transporting device, with rectification properties (diode) was prepared with the following layer structure:
 a. 90 nm ITO (indium tin oxide) as anode
 b. 40 nm 2,9-di(biphenyl-4-yl)-4,7-diphenyl-1,10-phenanthroline
 c. 2 nm layer of compound (10)
 d. 15 nm Mg:Al (10 vol %) or 50 nm Al as cathode Comparative examples where made using the strong donor W(hpp)2, the results show that both structures are rectifying and the current injection efficiency is very similar. The advantage of using the compounds of Formula (I) are clear, those compounds are, contrary to W(hpp)2, highly stable against degradation, and even stable in air.

|  | Mg:Al | Al |
| --- | --- | --- |
| W(hpp)2 | 2.685 | 3.075 |
| Compound (10) | 2.68 | 2.925 |

Table showing the median voltage of the devices above at a current density of 10 mA/cm2.

Example 1.2 pn Junction

A pn junction device was made with compound (23) using the following device structure:
 a. 90 nm ITO as anode
 b. 5 nm layer of compound (23) and Mg (5 mol % of Mg)
 c. 40 nm α-NPD (N,N'-Bis(naphthalen-1-yl)-N,N'-bis(phenyl)-benzidine) 6 mol % doped with F6-TNAP (2,2'-(perfluoronaphthalene-2,6-diylidene)dimalononitrile)
 d. 40 nm α-NPD
 e. 100 nm Al as cathode The forward voltage at a current density of 5 mA/cm2 was about 6 V.

Another pn junction device was made with compound (10) using the following device structure:
 a. 90 nm ITO as anode
 b. 5 am layer of compound (10) and Mg (5 mol % of Mg)
 c. 5 nm of tetrakis(quinoxalin-5-yloxy)zirconium
 d. 40 nm α-NPD (N,N'-Bis(naphthalen-1-yl)-N,N'-bis(phenyl)-benzidine) 6 mol % doped with 2,2',2"-(cyclopropane-1,2,3-triylidene)tris(2-(p-cyanotetrafluorophenyl)acetunitrile)
 c. 40 nm α-NPD
 f. 100 am Al as cathode The forward voltage at a current density of 5 mA/cm2 was about 5.8 V.

A third pn junction device was made with the following device structure:
 a. 90 am ITO as anode
 b. 2 nm layer of compound (10)
 c. 2 nm of Al
 d. 40 nm α-NPD (N,N'-Bis(naphthalen-1-yl)-N,N'-bis(phenyl)-benzidine) 6 mol % doped with 2,2',2"-(cyclopropane-1,2,3-triylidene)tris(2-(p-cyanotetrafluorophenyl)acetonitrile)
 e. 40 nm α-NPD
 f. 100 nm Al as cathode The forward voltage at a current density of 5 mA/cm2 was about 5.3 V.

Example 2.1

OLED with Injection Layer

An OLED was prepared with the following layer structure on a glass substrate:
 a. 100 nm Ag as anode
 b. 40 nm α-NPD (N,N'-Bis(naphthalen-1-yl)-N,N'-bis(phenyl)-benzidine) doped with 3 mol % of F6-TNAP
 c. 100 nm α-NPD
 d. 20 nm doped blue emitter system
 e. 36 nm 2,9-di(biphenyl-4-yl)-4,7-diphenyl-1,10-phenanthroline
 f. (i) 2 nm layer of compound (10); (ii) 2 nm of W(hpp)2
 g. 12 nm Mg:Ag (10% vol)
 h. 60 nm α-NPD The results are similar as using an n-dopant interlayer such as W(hpp)2 in place of layer f.

|  | (i) | (ii) |
| --- | --- | --- |
| Quantum efficiency at 1000 cd/m2 | 7.0 | 5.0 |
| Voltage at a forward current density of 10 mA/cm2 | 3.4 V | 3.4 V |

Other comparative devices were fabricated without layer (f) and modifying the thickness of layer (e) to 38 nm. Additional comparative devices were fabricated replacing layer f) with 2 nm bathophenanthrolin (BPhen). Both types of comparative devices showed extremely poor performance; the voltage for a current density of 1 mA/cm2 was over 10 V.

The inventive OLED shows a lower operating voltage and a higher power efficiency demonstrating the high injection ability of the injection layer.

Example 2.2

An OLED was made according to example 2.1, wherein the injection layer was made 2 nm thick and formed by co-evaporating compound (24) and Mg with a molar ratio 5% (Mg in compound). A comparative OLED was made with the same device structure without an injection layer but with a 2 nm thicker ETL. The inventive OLED had considerable better performance, similar to the inventive device in example 1, wherein the comparative OLED only showed a current density of 1 mA/cm2 at 10 V.

Example 2.3

An OLED was made with the following layer structure on a glass substrate:
a. 90 nm ITO as anode
b. 2 nm 2,2'-(perfluoronaphthalene-2,6-diylidene)dimalononitrile
c. 40 nm of α-NPD
d. 20 nm blue emitter system
e. 10 nm 2,9-di(biphenyl-4-yl)-4,7-diphenyl-1,10-phenanthroline
f. 40 nm of a matrix 2,9-di(biphenyl-4-yl)-4,7-diphenyl-1,10-phenanthroline doped with compound (10) and Mg with the following concentration 75:5:20 wt % (matrix:Mg:compound (10))
g. 100 nm Al as cathode The OLED showed a low voltage of only 3.3 V at 10 mA/cm2 and a current efficiency over 10 cd/A. Another device was made with the same stack however as inverted structure, (the cathode formed first, and closer to the substrate than the anode).

Example 2.4

An OLED was made according to example 3 wherein an additional layer with a thickness of 5 nm comprising compound (10) and Mg with a weight ratio 1:5 (Mg:compound (23)) was formed between the ETL and the cathode. The OLED had a slightly increased power performance compared to the example 3 and a small increase in lifetime.

Solar Cells

Example 3.1

Organic Solar Cell with Injection Layer

An organic solar cell was fabricated with the following procedure: patterned glass substrate coated with ITO was cleaned in an ultrasound bath with ethanol, acetone and isopropanol. Afterwards the ITO substrate was exposed to oxygen plasma treatment for 15 minutes. The substrate was loaded into the vacuum through of a glove box with nitrogen. In vacuum the organic layers were deposited with conventional VTE (vacuum thermal evaporation). First a 30 nm thick 5% (molar) p-doped Meo-TPD (tetrakis(4-methoxyphenyl) biphenyl-4,4'-diamine) was deposited through a shadow mask over the ITO followed by a 10 nm undoped ZnPc (zinc phthalocyanine) layer. A 30 nm thick mixed layer of fullerene C60 and ZnPc was deposited with a molar ratio of 2(C60):1 (CuPc). A 40 nm thick C60 layer was deposited on top of the mixed layer. An injection layer of 2.5 nm (compound 11) layer was deposited on top of the C60 layer. The compound (10) layer is followed by a 100 nm thick Al cathode. Although under normal operation, the cathode extracts electrons from the organic semiconducting layer, the solar cell still has a conventional diode behaviour in dark and also under forward bias; therefore the compound (10) layer is still called an injection layer.

In a comparative example, the ETL was made thicker by 2.5 nm and no injection layer was used. In another comparative example, an organic solar cell was made according to the example 6, however the injection layer was replaced by a BPhen buffer layer with thickness of 2.5 nm. The inventive organic solar cell shows a lower operating voltage and a higher power efficiency showing that the injection layer according to the invention is not simply a buffer layer.

Example 3.2

An organic solar cell was made according to example 3.1 wherein an additional layer with a thickness of 2 nm comprising of compound compound (10) and Mg with a doping weight ratio 5:1 (compound (10):Mg) was formed between the ETL and the cathode. The organic solar cell had a slight increased power performance compared to the example 8 and also a increase in lifetime.

Example 4

OTFT

An ITO layer was formed on a glass substrate as a gate electrode. Subsequently an 800 nm thick polymethylmethacrylate (PMMA) layer was formed by spin-coating a solution on the ITO layer to serve as gate insulator. A 50 nm thick perfluoropentacene layer was deposited over the gate insulator by VTE. An unpatterned injection layer of 2 nm compound (10) was deposited over the perfluoropentacene layer by VTE, and the source and drain electrodes made of Al were deposited on top of the injection layer. The channel length was 3 mm and its width was 50 nm. A comparative example was made using F6-TNAP as unstructured injection layer, the comparative example had a more than 15× increased off current, and a 10× smaller on/off ratio compared to the inventive device. A comparative example without any injection layer was also made having an off current similar to the inventive device but a 100× smaller on/off ratio,

Example 5

Solution Processing

A polymer OLED was made with the following device structure on an ITO pre coated glass substrate:

40 nm spin-coated PEDOT-PSS 60 nm of a polyfluorene derivative (spin coated)

2 nm of compound (10)

Mg (10 nm)/Al (100 nm)

A comparative device without the compound (10) layer showed inferior performance than the inventive device.

In a separated test it was found that layers of the inventive devices can be made by ink-jet printing.

The features disclosed in the foregoing description, in the drawing or in the claims may, both separately and in any combination thereof, be material for realizing the invention in diverse forms thereof.

The invention claimed is:
1. A chemical compound according to formula (I):

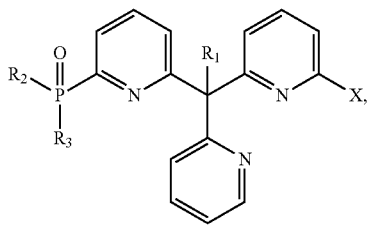

wherein X is selected from H or formula (I.2),

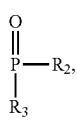

wherein $R_2$ and $R_3$ are independently selected from the group consisting of H, linear alkyl, branched alkyl, aryl, and heteroaryl; and
wherein $R_1$ is independently selected from the group consisting of linear alkyl, branched alkyl, aryl, and heteroaryl.

2. The chemical compound according to claim 1, wherein $R_1$, $R_2$, and $R_3$ are independently selected from $C_1$-$C_6$ alkyl, $C_6$-$C_{20}$ aryl, or $C_5$-$C_{20}$ heteroaryl.

3. An organic electronic device comprising at least one substantially organic layer comprising a chemical compound according to formula (I):

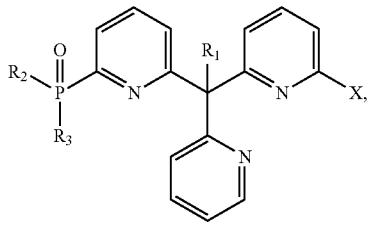

wherein X is selected from H or formula (I.2)

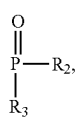

wherein $R_2$ and $R_3$ are independently selected from the group consisting of H, linear alkyl, branched alkyl, aryl, and heteroaryl; and
wherein $R_1$ is independently selected from the group consisting of linear alkyl, branched alkyl, aryl, and heteroaryl.

4. The organic electronic device according to claim 3, wherein the substantially organic layer comprises at least one metal or a metal ion.

5. The organic electronic device according to claim 3, comprising a layered structure, wherein the layered structure comprises a substrate, an anode, and a cathode, and wherein the at least one substantially organic layer is arranged within the layered structure between the anode and the cathode.

6. The organic electronic device according to claim 5, wherein the cathode is a top electrode and the anode is a bottom electrode, wherein the bottom electrode is closer to the substrate than the top electrode.

7. The organic electronic device according to claim 5, wherein the substantially organic layer has an interface with the cathode.

8. The organic electronic device according to claim 3, wherein the substantially organic layer further comprises an electron transport material.

9. The organic electronic device according to claim 3, wherein the substantially organic layer comprises at least part of a pn junction, the pn junction comprising at least a p-layer and an n-layer.

10. The organic electronic device according to claim 3, further comprising a polymer semiconducting layer.

11. The organic electronic device according to claim 3, wherein the organic electronic device is a solar cell or a light emitting diode.

12. The organic electronic device according to claim 3, wherein the organic electronic device is a field effect transistor comprising a semiconducting channel, a source electrode, and a drain electrode, wherein the substantially organic layer is arranged between the semiconducting channel and at least one of the source electrode and the drain electrode.

13. The organic electronic device according to claim 3, wherein the substantially organic layer is an electron injection layer or an n-doped electron transport layer.

14. The organic electronic device according to claim 4, wherein the metal or metal ion is capable of interacting with the chemical compound according to formula (I).

15. The organic electronic device according to claim 4, wherein the metal or metal ion is selected from Ag, Al, Mg, Ba, Ca, Yb, In, Zn Sn, Sm, Bi, Eu, or Li.

16. The organic electronic device according to claim 9, wherein the device further comprises an interlayer i arranged between the player and the n-layer.

17. The organic electronic device according to claim 16, wherein the interlayer i or the n-layer comprises the substantially organic layer.

18. A process for preparing an organic electronic device comprising:
depositing a substantially organic layer comprising a chemical compound according to formula (I) on a first other layer, and
depositing a second other layer on the substantially organic layer, wherein the compound according to formula (I) has the following structure

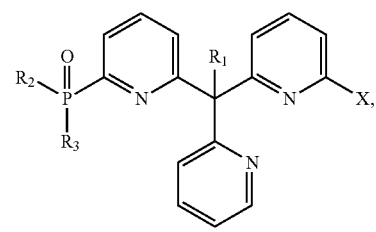

wherein X is selected from H or formula (I.2),

wherein $R_2$ and $R_3$ are independently selected from the group consisting of H, linear branched alkyl, aryl, and heteroaryl; and $R_1$ is independently selected from the group consisting of linear alkyl., branched alkyl aryl, and heteroaryl.

19. The process according to claim 18, wherein depositing the substantially organic layer comprises evaporating the substantially organic layer.

20. The process according to claim 18, wherein the organic semiconducting layer is deposited from a solution.

21. The process according to claim 18, wherein the second other layer comprises a cathode.

22. The process according to claim 19, wherein evaporating comprises co-evaporating the substantially organic layer with a metal or electron transport material.

* * * * *

UNITED STATES PATENT AND TRADEMARK OFFICE
CERTIFICATE OF CORRECTION

PATENT NO. : 8,778,512 B2  
APPLICATION NO. : 13/291169  
DATED : July 15, 2014  
INVENTOR(S) : Sascha Dorok et al.

Page 1 of 1

It is certified that error appears in the above-identified patent and that said Letters Patent is hereby corrected as shown below:

In the Claims:

At column 22, line 43, delete "player" and insert -- p-layer --.

Signed and Sealed this
Sixteenth Day of September, 2014

Michelle K. Lee
*Deputy Director of the United States Patent and Trademark Office*